United States Patent [19]

Nadelson

[11] 4,158,735

[45] Jun. 19, 1979

[54] SUBSTITUTED HYDROXY PYRIDONES

[75] Inventor: Jeffrey Nadelson, Denville, N.J.

[73] Assignee: Sandoz, Inc., E. Hanover, N.J.

[21] Appl. No.: 901,477

[22] Filed: May 1, 1978

Related U.S. Application Data

[60] Division of Ser. No. 760,818, Jan. 19, 1977, Pat. No. 4,103,013, which is a continuation-in-part of Ser. No. 719,231, Aug. 31, 1976, abandoned, which is a continuation-in-part of Ser. No. 625,817, Oct. 28, 1975, abandoned, which is a continuation-in-part of Ser. No. 584,764, Jun. 9, 1975, abandoned, which is a continuation-in-part of Ser. No. 558,419, Mar. 14, 1975, abandoned.

[51] Int. Cl.$^2$ .......................................... C07D 498/14
[52] U.S. Cl. .............................. 546/116; 260/307 H

[58] Field of Search ............ 260/295 L, 296 H, 307 H

[56] References Cited

U.S. PATENT DOCUMENTS

| 4,024,262 | 5/1977 | Nadelson | 424/263 |
| 4,103,013 | 7/1978 | Nadelson | 424/263 |
| 4,122,182 | 10/1978 | Nadelson | 424/263 |

*Primary Examiner*—John D. Randolph
*Attorney, Agent, or Firm*—Gerald D. Sharkin; Robert S. Honor; Timothy G. Rothwell

[57] ABSTRACT

Substituted hydroxy pyridones, e.g., 3-(α-iminobenzyl)-4-hydroxy-6-phenyl-1-methyl-2(1H)-pyridone, are prepared by reducing corresponding isoxazolo[4,5-c]pyridin-4(5H)-ones and are useful as minor tranquilizers and sleep inducers.

2 Claims, No Drawings

SUBSTITUTED HYDROXY PYRIDONES

This is a division of application Ser. No. 760,818, filed Jan. 19, 1977, now U.S. Pat. No. 4,103,013, issued July 25, 1978, which in turn is a continuation-in-part of copending application Ser. No. 719,231 filed Aug. 31, 1976, now abandoned which in turn is a continuation-in-part of copending application Ser. No. 625,817, filed Oct. 28, 1975, now abandoned, which in turn is a continuation-in-part of copending application Ser. No. 584,764, filed June 9, 1975, now abandoned, which in turn is a continuation-in-part of copending application Ser. No. 558,419, filed Mar. 14, 1975, now abandoned.

This invention relates to substituted hydroxy pyridones which exhibit minor tranquilizer and sleep inducer activity. In particular, it relates to 4-hydroxy-6-substituted or unsubstituted phenyl-1-substituted-2(1H)-pyridones, intermediates thereof, pharmaceutically acceptable salts, and to methods for their preparation.

The compounds of this invention may be represented by the following structural formula:

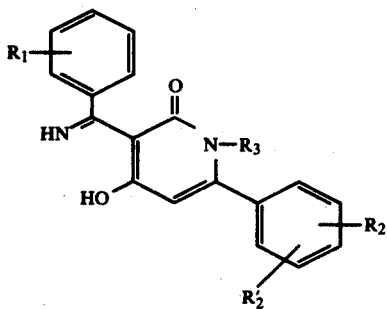
(I)

wherein $R_1$, $R_2$ and $R_2'$ each independently represent hydrogen, halo having an atomic weight of about 19 to 36, lower alkyl, i.e., alkyl having 1 to 4 carbon atoms, e.g., methyl, ethyl, isopropyl and the like, lower alkoxy, i.e., alkoxy having 1 to 4 carbon atoms, e.g., methoxy, ethoxy and the like, or trifluoromethyl, and $R_3$ represents lower alkyl as defined above.

The compounds of formula (I) are prepared according to the following reaction scheme:

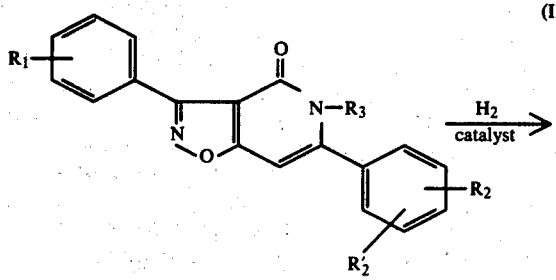
(II)

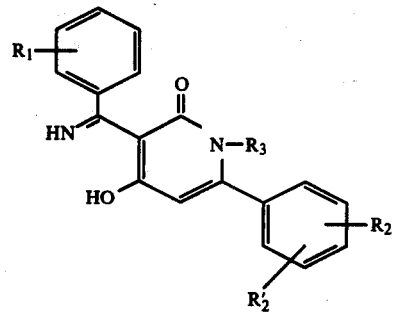
(I)

where $R_1$, $R_2$, $R_2'$ and $R_3$ are as defined above.

The compounds of formula (I) are prepared by reducing a compound of the formula (II) under hydrogen gas in the presence of a catalyst and an inert organic solvent. Although the particular catalyst employed is not critical, the preferred catalysts include palladium on carbon, platinum oxide, raney nickel, and the like, preferably palladium on carbon. The particular solvent used is not critical, but it is preferred that the reaction be run in the presence of the lower alkanols, e.g., methanol, ethanol, and the like, preferably ethanol. The temperature of the reaction is not critical, but it is preferred that the reaction be run from about 10° to 50° C., preferably from about 20° to 30° C. The reaction is run from about 1 to 10 hours, preferably from about 2 to 3 hours. The product is recovered using conventional techniques, e.g., filtration.

The compounds of formula (II) are prepared according to the following reaction scheme:

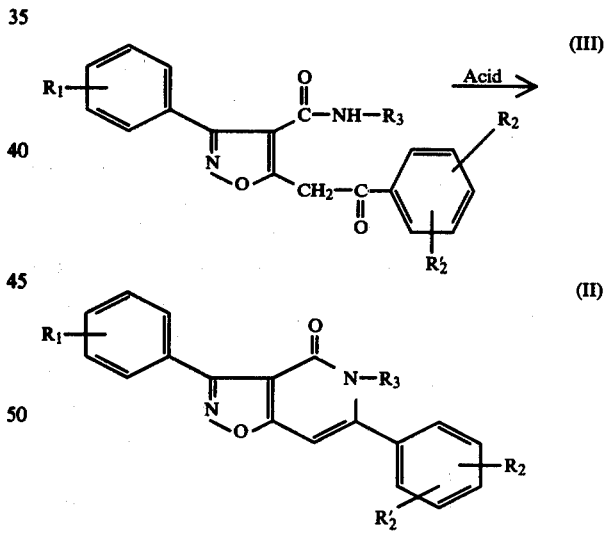

where $R_1$, $R_2$ $R_2'$ and $R_3$ are as defined above.

The compounds of formula (II) are prepared by treating a compound of the formula (III) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being especially preferred. The temperature of the reaction is not critical, but it is preferred that the reaction be run from about 80° to 150° C., preferably the reflux temperature of the solvent.

The reaction is run from about 12 to 36 hours, preferably from about 20 to 36 hours. The product is recovered using conventional techniques, e.g., trituration followed by recrystallization.

The compounds of formula (III) are prepared according to the following reaction scheme:

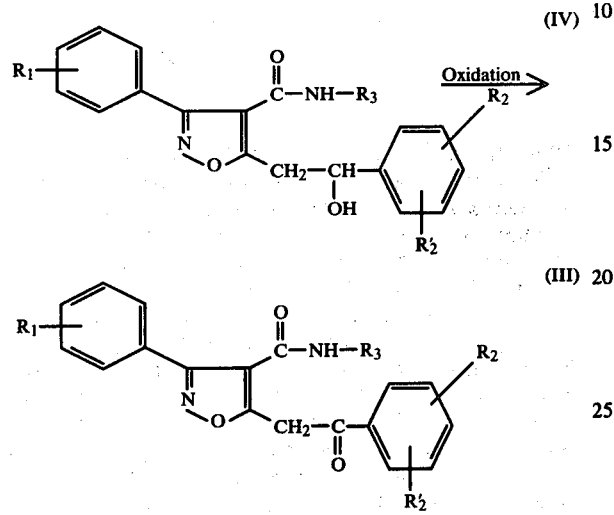

where $R_1$, $R_2$, $R_2'$ and $R_3$ are as defined above.

The compounds of formula (III) are prepared by treating a compound of the formula (IV) with an oxidizing agent such as chromium trioxide, potassium permanganate, and the like, preferably chromium trioxide, under acidic conditions in the presence of water. Although the particular acid employed is not critical, the preferred acids include the mineral acids such as sulfuric acid, hydrochloric acid or acetic acid, the latter being especially preferred. The particular solvent employed is critical, and water is the only solvent contemplated in this reaction. The temperature of the reaction is not critical, but it is preferred that the reaction be run from about 10° to 50° C., preferably from about 20° to 30° C. The reaction is run from about 1 to 5 hours, preferably from about 1.5 to 2.5 hours. The product is recovered using conventional techniques, e.g., trituration followed by filtration.

The compounds of formula (IV) may be prepared according to the following reaction scheme:

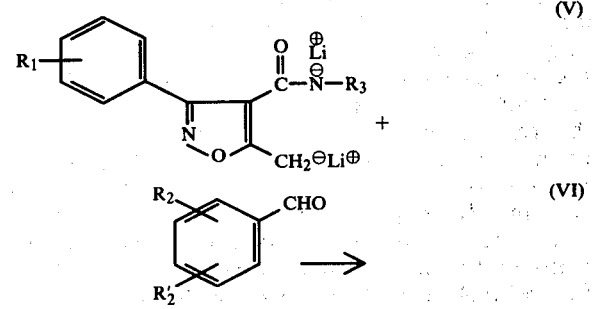

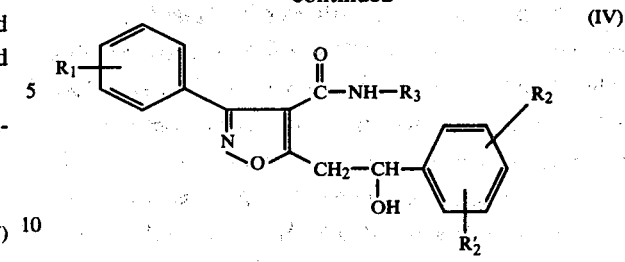

where $R_1$, $R_2$, $R_2'$ and $R_3$ are as defined above.

The compounds of formula (IV) are prepared by treating a compound of the formula (V) with a compound of the formula (VI) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably tetrahydrofuran. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product is recovered using conventional techniques, e.g., trituration followed by filtration.

The compounds of formula (V) may be prepared according to the following reaction scheme:

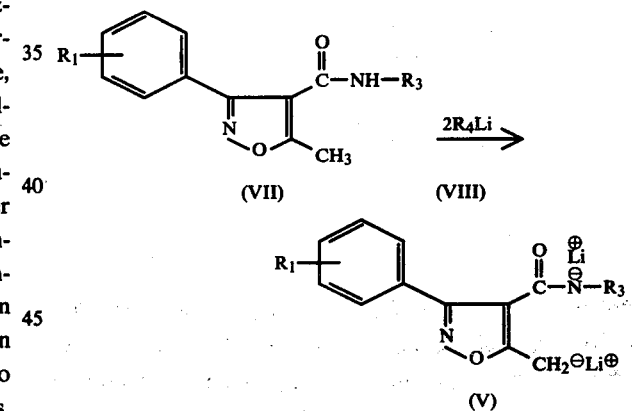

where
$R_4$ is lower alkyl having 1 to 4 carbon atoms, and
$R_1$ and $R_3$ are as defined above.

The compounds of formula (V) are prepared by treating a compound of the formula (VII) with a compound of the formula (VIII) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably hexane. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product of the compound of formula (VII) is not isolated but employed in situ as a starting material in the preparation of the compounds of formula (IV).

The compound of formula (I) may also exist in the following tautomeric forms, and these tautomeric forms are also included within the scope of this invention.

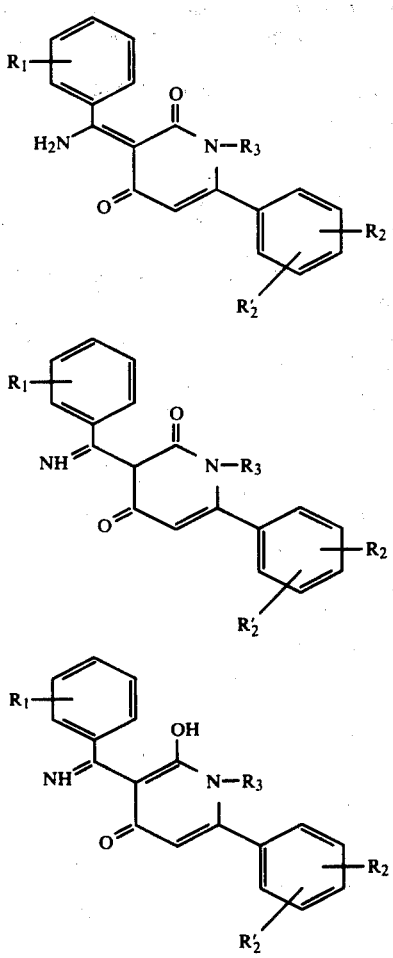

where $R_1$, $R_2$, $R_2'$ and $R_3$ are as defined above.

Many of the compounds of formulae (VI), (VII) and (VIII) are known and may be prepared by methods described in the literature. The compounds of formulae (VI), (VII), and (VIII) not specifically described may be prepared by analogous methods from known starting materials.

The compounds of formula (I) are useful because they possess pharmacological activity in animals as sleep inducers and minor tranquilizers as indicated (1) by the hexobarbital reinduction method of Winter, J. Pharmacol, and Exp. Therap., 94, 7-11, 1948; (2) by their ability to produce docility in behavior tests in mice given 25 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chronic convulsions and death in mice given about 35 mg/kg of the test compound followed immediately by 45 to 250 mg/kg i.p. of N-sulfamoylazepine; (4) by scoring for loss of righting reflex according to the method of Reed-Muench (American Journal of Hygiene, 27: 493-497, 1938), in which mice are administered 12.5 mg/kg, i.p. Thioridazine, immediately after which the test compound is administered at dosages of 5 to 100 mg/kg in a volume of 0.1 ml/10 g. body weight. Sixty minutes after dosing, the mice are scored for loss of righting reflex and (5) by their ability to reduce conflicts as defined in the Geller Conflict test (Irving Geller, Psychopharmacologia, Vol. 1, page 42-492 (1960).

Certain of the compounds of formula (I) wherein $R_1$, $R_2$ and $R_2'$ each independently represent halo having an atomic weight of about 19 to 36 also exhibit pharmacological activity as muscle-relaxants as indicated (1) by their activity in the rotorod test as described by Dunham and Miya (J. Am. Pharm. Assoc., 45: 208, 1957), (2) by their ability to depress spinal reflexes measured by flexor and patellar responses using force displacement transducers in male cats given 0.1 to 3.0 milligrams per kilogram of animal body weight, i.v. of the test compound and (3) by their ability to depress electrically evoked mono-synapatic and/or poly-synapatic reflexes in male cats given 1 to 30 milligrams per kilogram of animal body weight i.v. of the test compound.

The sleep inducing effective dosage of the compounds of formula (I) will vary depending on the particular compound employed. However, in general, satisfactory results are obtained when the compounds are administered orally at a daily dosage of from about 0.5 milligrams to about 200 milligrams per kilogram of animal body weight, typically given in a single dose at bedtime. For most large mammals, the total daily dosage is from about 30 to about 1500 milligrams, preferably at bedtime and dosage forms suitable for internal administration comprise from about 7.5 to about 750 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

For minor tranquilizer use in the treatment of anxiety and tension, the effective dosage will vary depending on the particular compound employed. However, in general, satisfactory results are obtained when the compounds are administered orally at a daily dosage of from about 0.2 milligrams to about 200 milligrams per kilogram of animal body weight, typically given in divided doses two to four times per day. For most large mammals, the total daily dosage is from about 10 to about 1500 milligrams, and dosage forms suitable for internal administration comprise from about 2.5 to about 750 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compounds are administered orally at a daily dosage of from about 0.1 milligrams to about 200 milligrams per kilogram of animal body weight typically given in divided doses two to four times per day. For most large mammals, the total daily dosage is from about 1.0 to about 1500 milligrams and dosage forms suitable for internal administration comprise from about 0.25 to about 750 milligrams of the compound in admixture with a solid or liquid pharmaceutical carrier or diluent.

The compounds of formula (I) may be similarly administered in the form of their non-toxic pharmaceutically acceptable salts. Such salts possess the same order of activity as the free acid and are readily prepared by reacting the compound with a pharmaceutically acceptable base by conventional technique and, accordingly, are included within the scope of this invention. Representative of such salts are the alkali metal salts, e.g., salts with lithium, sodium, potassium and the like, and the alkali earth metal salts such as salts with magnesium, calcium and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.) | |
|---|---|---|
| | tablet | capsule |
| 3-(αiminobenzyl)-4-hydroxy-6-phenyl-1-methyl-2-(1H)-pyridone | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

3-Phenyl-5-(β-hydroxyphenethyl)-N-methyl-isoxazole-4-carboxamide.

A suspension of 75 g. (0.348 mole) of 3-phenyl-5,N-dimethyl-isoxazole-4-carboxamide and 1 liter of tetrahydrofuran is cooled to −65° C. and 478 ml. of 1.6 M n-butyllithium in hexane (0.765 mole) is added dropwise maintaining the temperature between −60° and −70° C. After the addition is complete, the orange suspension is stirred for 1½ hours at −60° to −70° C., and then 37.2 g. (0.350 mole) of benzaldehyde in 375 ml. tetrahydrofuran is added dropwise maintaining the temperature between −60° and −70° C. After addition is complete the mixture is stirred 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered and evaporated in vacuo. The solid residue is triturated with a 50:50 mixture of ether:petroleum ether, filtered and washed with cold ether to give 3-phenyl-5-(β-hydroxyphenethyl)-N-methyl-isoxazole-4-carboxamide, m.p. 183°–184° C.

Following the above procedure and using in place of 3-phenyl-N-methyl-isoxazole-4-carboxamide, an equivalent amount of (a) 3-(p-chlorophenyl)-5,N-dimethyl-isoxazole-4-carboxamide,
(b) 3-(p-fluorophenyl)-5,N-dimethyl-isoxazole-4-carboxamide,
(c) 3-(p-tolyl)-5,N-dimethyl-isoxazole-4-carboxamide,
(d) 3-(p-anisyl)-5,N-dimethyl-isoxazole-4-carboxamide, or
(e) 3-(m-trifluoromethylphenyl)-5,N-dimethyl-isoxazole-4-carboxamide, there is obtained
(a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide,
(c) 3-(p-tolyl)-5-(β-hydroxyphenethyl)-N-methyl-isoxazole-4-carboxamide,
(d) 3-(p-anisyl)-5-(β-hydroxyphenethyl)-N-methyl-isoxazole-4-carboxamide, or
(e) 3-(m-trifluoromethylphenyl)-5-(β-hydroxyphenethyl)-N-methyl-isoxazole-4-carboxamide, respectively.

Again following the same procedure and using in place of benzaldehyde an equivalent amount of
(f) p-chlorobenzaldehyde,
(g) p-fluorobenzaldehyde,
(h) p-methylbenzaldehyde,
(i) p-methoxybenzaldehyde,
(j) m-trifluoromethylbenzaldehyde,
(k) o-methylbenzaldehyde, or
(l) 3,4-dichlorobenzaldehyde, there is obtained
(f) 3-phenyl-5-(4-chloro-β-hydroxyphenethyl)-N-methyl-isoxazole-4-carboxamide,
(g) 3-phenyl-5-(4-fluoro-β-hydroxyphenethyl)-N-methyl-isoxazole-4carboxamide,
(h) 3-phenyl-5-(4-methyl-β-hydroxyphenethyl)-N-methyl-isoxazole-4-carboxamide,
(i) 3-phenyl-5-(4-methoxy-β-hydroxyphenethyl)-N-methyl-isoxazole-4-carboxamide,
(j) 3-phenyl-5-(3-trifluoromethyl-β-hydroxyphenethyl)-N-methyl-isoxazole-4-carboxamide,
(k) 3-phenyl-5-(2-methyl-β-hydroxyphenethyl)-N-methyl-isoxazole-4-carboxamide,
(l) 3-phenyl-5-(3,4-dichloro-β-hydroxyphenethyl)-N-methyl-isoxazole-4-carboxamide.

Also following the above procedure and using in place of 3-phenyl-5,N-dimethyl-isoxazole-4-carboxamide an equivalent amount of
(m) 3-(p-chlorophenyl)-5,N-dimethyl-isoxazole-4-carboxamide,
(n) 3-(p-fluorophenyl)-5,N-dimethyl-isoxazole-4-carboxamide,
(o) 3-(o-fluorophenyl)-5,N-dimethyl-isoxazole-4-carboxamide, and in place of benzaldehyde an equivalent amount of
(m) p-chlorobenzaldehyde,
(n) p-fluorobenzaldehyde,
(o) o-fluorobenzaldehyde
there is obtained
(m) 3-(p-chlorophenyl)-5-(4-chloro-β-hydroxyphenethyl)-N-methyl-isoxazole-carboxamide,
(n) 3-(p-fluorophenyl)-5-(4-fluoro-β-hydroxyphenethyl)-N-methyl-isoxazole-carboxamide, or
(o) 3-(o-fluorophenyl)-5-(4-fluoro-β-hydroxyphenethyl)-N-methyl-isoxazole-carboxamide, respectively.

Following the procedure of Example 1 and if an equivalent amount of 3,4-difluorobenzaldehyde is employed in place of benzaldehyde, there is obtained (p) 3-phenyl-5-(3,4-difluoro-β-hydroxyphenethyl)-N-methyl-isoxazole-4-carboxamide.

Also following the procedure of the above-mentioned example and using in place of 3-phenyl-N-methyl-isoxazole-4-carboxamide, an equivalent amount of 3-(o-fluorophenyl)-5,N-dimethyl-isoxazole-4-carboxamide there is obtained (g) 3-(o-fluorophenyl)-5-(β-hydroxyphenethyl)-N-methyl-isoxazole-carboxamide.

EXAMPLE 2

N-methyl-5-phenacyl-3-phenyl-4-isoxazole carboxamide.

A suspension of 50 g. (0.155 mole) of 3-phenyl-5-(β-hydroxyphenethyl)-N-methyl-isoxazole-4-carboxamide and 800 ml. acetic acid at room temperature is treated dropwise rapidly with 18.4 g. (0.185 mole) of chromium trioxide in 185 ml. water. The resulting solution is stirred for 2 hours at room temperature and a portion of the acetic acid is removed in vacuo. The remainder is poured onto ice water and extracted with methylene chloride. The methylene chloride layer is washed with 2 N sodium hydroxide, dried over anhydrous magnesium sulfate, filtered and evaporated in vacuo. The solid residue is triturated with hot ether, cooled to 0° C. and filtered to give N-methyl-5-phenacyl-3-phenyl-4-isoxazole carboxamide, m.p. 125° to 128° C.

Following the above procedure and using in place of 3-phenyl-5-(β-hydroxyphenethyl)-N-methyl-isoxazole-4-carboxamide, an equivalent amount of (a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide,
(c) 3-(p-tolyl)-5-(β-hydroxyphenethyl)-N-methyl-isoxazole-4-carboxamide,
(d) 3-(p-anisyl)-5-(β-hydroxyphenethyl)-N-methyl-isoxazole-4-carboxamide,
(e) 3-(m-trifluoromethylphenyl)-5-(β-hydroxyphenethyl)-N-methyl-isoxazole-4-carboxamide,
(f) 3-phenyl-5-(4-chloro-β-hydroxyphenethyl)-N-methyl-isoxazole-4-carboxamide,
(g) 3-phenyl-5-(4-fluoro-β-hydroxyphenethyl)-N-methyl-isoxazole-4-carboxamide,
(h) 3-phenyl-5-(4-methyl-β-hydroxyphenethyl)-N-methyl-isoxazole-4-carboxamide,
(i) 3-phenyl-5-(4-methoxy-β-hydroxyphenethyl)-N-methyl-isoxazole-4-carboxamide,
(j) 3-phenyl-5-(3-trifluoromethyl-β-hydroxyphenethyl)-N-methyl-isoxazole-4-carboxamide,
(k) 3-phenyl-5-(2-methyl-β-hydroxyphenethyl)-N-methyl-isoxazole-4-carboxamide,
(l) 3-phenyl-5-(3,4-dichloro-β-hydroxyphenethyl)-N-methyl-isoxazole-4-carboxamide,
(m) 3-(p-chlorophenyl)-5-(4-chloro-β-hydroxyphenethyl)-N-methyl-isoxazole-4-carboxamide,
(n) 3-(p-fluorophenyl)-5-(4-fluoro-β-hydroxyphenethyl)-N-methyl-isoxazole-4-carboxamide,
(o) 3-(o-fluorophenyl)-5-(4-fluoro-β-hydroxyphenethyl)-N-methyl-isoxazole-4-carboxamide,
(p) 3-phenyl-5-(3,4-difluoro-β-hydroxyphenethyl)-N-methyl-isoxazole-4-carboxamide, or
(q) 3-(p-fluorophenyl)-5-(p-hydroxyphenethyl)-N-methyl-isoxazole-4-carboxamide there is obtained (a) N-methyl-5-phenacyl-3-(p-chlorophenyl)-4-isoxazole carboxamide,
(b) N-methyl-5-phenacyl-3-(p-fluorophenyl)-4-isoxazole carboxamide,
(c) N-methyl-5-phenacyl-3-(p-tolyl)-4-isoxazole carboxamide,
(d) N-methyl-5-phenacyl-3-(p-anisyl)-4-isoxazole carboxamide,
(e) N-methyl-5-phenacyl-3-(m-trifluoromethylphenyl)-4-isoxazole carboxamide,
(f) N-methyl-5-(4-chlorophenacyl)-3-phenyl-4-isoxazole carboxamide,
(g) N-methyl-5-(4-fluorophenacyl)-3-phenyl-4-isoxazole carboxamide,
(h) N-methyl-5-(4-methylphenacyl)-3-phenyl-4-isoxazole carboxamide,
(i) N-methyl-5-(4-methoxyphenacyl)-3-phenyl-4-isoxazole carboxamide,
(j) N-methyl-5-(3-trifluoromethylphenacyl)-3-phenyl-4-isoxazole carboxamide,
(k) N-methyl-5-(2-methylphenacyl)-3-phenyl-4-isoxazole carboxamide,
(l) N-methyl-5-(3,4-dichlorophenacyl)-3-phenyl-4-isoxazole carboxamide,
(m) N-methyl-5-(4-chlorophenacyl)-3-(p-chlorophenyl)-4-isoxazole carboxamide,
(n) N-methyl-5-(4-fluorophenacyl)-3-(p-fluorophenyl)-4-isoxazole carboxamide,
(o) N-methyl-5-(2-fluorophenacyl)-3-(p-fluorophenyl)-4-isoxazole carboxamide,
(p) N-methyl-5-(3,4-difluorophenacyl)-3-phenyl-4-isoxazole carboxamide, or
(q) N-methyl-5-phenacyl-3-(o-fluorophenyl)-4-isoxazole carboxamide, respectively.

EXAMPLE 3

5-Methyl-3,6-diphenyl-isoxazolo[4,5-c]pyridin-4(5H)-one.

A mixture of 26.1 g (0.0815 mole) of N-methyl-5-phenacyl-3-phenyl-4-isoxazole carboxamide and 261 ml. of 2 M sulfuric acid is refluxed for 24 hours. The mixture is cooled and extracted with methylene chloride. The methylene chloride layer is washed with water and then brine, dried over anhydrous magnesium sulfate, filtered and evaporated in vacuo. The residue is triturated with ether and then recrystallized from ethanol to give 5-methyl-3,6-diphenylisoxazolo[4,5-c]pyridin-4(5H)-one, m.p. 149°–151.5° C.

Following the above procedure and using in place of N-methyl-5-phenacyl-3-phenyl-4-isoxazole carboxamide, an equivalent amount of (a) N-methyl-5-phenacyl-3-(p-chlorophenyl)-4-isoxazole carboxamide,
(b) N-methyl-5-phenacyl-3-(p-fluorophenyl)-4-isoxazole carboxamide,
(c) N-methyl-5-phenacyl-3-(p-tolyl)-4-isxoazole carboxamide,
(d) N-methyl-5-phenacyl-3-(p-anisyl)-4-isoxazole carboxamide,
(e) N-methyl-5-phenacyl-3-(m-trifluoromethylphenyl)-4-isoxazole carboxamide,
(f) N-methyl-5-(4-chlorophenacyl)-3-phenyl-4-isoxazole carboxamide, (g) N-methyl-5-(4-fluorophenacyl)-3-phenyl-4-isoxazole carboxamide,
(h) N-methyl-5-(4-methylphenacyl)-3-phenyl-4-isoxazole carboxamide,
(i) N-methyl-5-(4-methoxyphenacyl)-3-phenyl-4-isoxazole carboxamide,
(j) N-methyl-5-(3-trifluoromethylphenacyl)-3-phenyl-4-isoxazole carboxamide,
(k) N-methyl-5-(2-methylphenacyl)-3-phenyl-4-isoxazole carboxamide,
(l) N-methyl-5-(3,4-dichlorophenacyl)-3-phenyl-4-isoxazole carboxamide, or
(m) N-methyl-5-(4-chlorophenacyl)-3-(p-chlorophenyl)-4-isoxazole carboxamide,
(n) N-methyl-5-(4-fluorophenyl)-3-(p-fluorophenyl)-4-isoxazole carboxamide,
(o) N-methyl-5-(2-fluorophenacyl)-3-(p-fluorophenyl)-4-isoxazole carboxamide,
(p) N-methyl-5-(3,4-difluorophenacyl)-3-phenyl-4-isoxazole carboxamide, or
(q) N-methyl-5-phenacyl-3-(p-fluorophenyl)-4-isoxazole carboxamide there is obtained
(a) 5-methyl-3-(p-chlorophenyl)-6-phenyl-isoxazolo[4,5-c]pyridin-4(5H)-one,
(b) 5-methyl-3-(p-fluorophenyl)-6-phenyl-isoxazolo[4,5-c]pyridin-4(5H)-one,
(c) 5-methyl-3-(p-tolyl)-6-phenyl-isoxazolo[4,5-c]pyridin-4(5H)-one,
(d) 5-methyl-3-(p-anisyl)-6-phenyl-isoxazolo[4,5-c]pyridin-4(5H)-one,
(e) 5-methyl-3-(m-trifluoromethylphenyl)-6-phenyl-isoxazolo[4,5-c]pyridin-4(5H)-one,
(f) 5-methyl-3-phenyl-6-(p-chlorophenyl)-isoxazolo[4,5-c]pyridin-4(5H)-one,
(g) 5-methyl-3-phenyl-6-(p-fluorophenyl)-isoxazolo[4,5-c]pyridin-4(5H)-one,
(h) 5-methyl-3-phenyl-6-(p-tolyl)-isoxazolo[4,5-c]pyridin-4(5H)-one,
(i) 5-methyl-3-phenyl-6-(p-anisyl)-isoxazolo[4,5-c]pyridin-4(5H)-one,
(j) 5-methyl-3-phenyl-6-(m-trifluoromethylphenyl)-isoxazolo[4,5-c]pyridin-4(5H)-one,
(k) 5-methyl-3-phenyl-6-(o-tolyl)-isoxazolo[4,5-c]pyridin-4(5H)-one,
(l) 5-methyl-3-phenyl-6-(3,4-dichlorophenyl)-isoxazolo[4,5-c]pyridin-4(5H)-one,
(m) 5-methyl-3-(p-chlorophenyl)-6-(p-chlorophenyl)-isoxazolo[4,5-c]pyridin-4(5H)-one,
(n) 5-methyl-3-(p-fluorophenyl)-6-(p-fluorophenyl)-isoxazolo[4,5-c]pyridin-4(5H)-one,
(o) 5-methyl-3-(o-fluorophenyl)-6-(p-fluorophenyl)-isoxazolo[4,5-c]pyridin-4(5H)-one,
(p) 5-methyl-3-phenyl-6-(3,4-difluorophenyl)-isoxazolo[4,5-c]pyridin-4(5H)-one, or
(q) 5-methyl-3-(o-fluorophenyl)-6-phenyl-isoxazolo[4,5-c]pyridin-4(5H)-one, respectively.

EXAMPLE 4

3-(α-iminobenzyl)-4-hydroxy-6-phenyl-1-methyl-2(1H)-pyridone.

A mixture of 16.5 g. (0.0545 mole) of N-methyl-3,6-diphenyl-isoxazolo[4,5-c]pyridin-4(5H)-one, 330 ml. ethanol and 1.65 g. 10% palladium on carbon is hydrogenated at 50 psi and room temperature. The hydrogenation is ceased after 1 equivalent of hydrogen is absorbed (ca 2.5 hours). The mixture is treated with methylene chloride and the catalyst is removed by filtration. The solvents are removed in vacuo to a volume of ca 50 ml. and then ether is added, to precipitate solids which are removed by filtration to give 3-(α-iminobenzyl)-4-hydroxy-6-phenyl-1-methyl-2(1H)-pyridone, m.p. 238°-240° C. The above compound is dissolved in methanol and treated with sodium hydroxide solution to yield after evaporation the sodium salt of 3-(α-iminobenzyl)-4-hydroxy-6-phenyl-1-methyl-2(1H)-pyridone.

Following the above procedure and using in place of 5-methyl-3,6-diphenyl-isozazolo[4,5-c]pyridin-4-(5H)-one, an equivalent amount of
(a) 5-methyl-3-(p-chlorophenyl)-6-phenyl-isoxazolo[4,5-c]pyridin-4(5H)-one,
(b) 5-methyl-3-(p-fluorophenyl)-6-phenyl-isoxazolo[4,5-c]pyridin-4(5H)-one,
(c) 5-methyl-3-(p-tolyl)-6-phenyl-isoxazolo[4,5-c]pyridin-4(5H)-one,
(d) 5-methyl-3-(p-anisyl)-6-phenyl-isoxazolo[4,5-c]pyridin-4(5H)-one,
(e) 5-methyl-3-(m-trifluoromethylphenyl)-6-phenyl-isoxazolo[4,5-c]pyridin-4(5H)-one,
(f) 5-methyl-3-phenyl-6-(p-chlorophenyl)-isoxazolo[4,5-c]pyridin-4(5H)-one,
(g) 5-methyl-3-phenyl-6-(p-fluorophenyl)-isoxazolo[4,5-c]pyridin-4(5H)-one,
(h) 5-methyl-3-phenyl-6-(p-tolyl)-isoxazolo[4,5-c]pyridin-4(5H)-one,
(i) 5-methyl-3-phenyl-6-(p-anisyl)-isoxazolo[4,5-c]pyridin-4(5H)-one,
(j) 5-methyl-3-phenyl-6-(m-trifluoromethylphenyl)-isoxazolo[4,5-c]pyridin-4(5H)-one,
(k) 5-methyl-3-phenyl-6-(o-tolyl)-isoxazolo[4,5-c]pyridin-4(5H)-one,
(l) 5-methyl-3-phenyl-6-(3,4-dichlorophenyl)-isoxazolo[4,5-c]pyridin-4(5H)-one,
(m) 5-methyl-3-(p-chlorophenyl)-6-(p-chlorophenyl)-isoxazolo[4,5-c]pyridin-4(5H)-one,
(n) 5-methyl-3-(p-fluorophenyl)-6-(p-fluorophenyl)-isoxazolo[4,5-c]pyridin-4(5H)-one,
(o) 5-methyl-3-(o-fluorophenyl)-6-(p-fluorophenyl)-isoxazolo[4,5-c]pyridin-4(5H)-one,
(p) 5-methyl-3-phenyl-6-(3,4-difluorophenyl)-isoxazolo[4,5-c]pyridin-4(5H)-one, or
(q) 5-methyl-3-(o-fluorophenyl)-6-phenyl-isoxazolo[4,5-c]pyridin-4(5H)-one, there is obtained
(a) 3-(α-imino-p-chlorobenzyl)-4-hydroxy-6-phenyl-1-methyl-2(1H)-pyridone,
(b) 3-(α-imino-p-fluorobenzyl)-4-hydroxy-6-phenyl-1-methyl-2(1H)-pyridone,
(c) 3-(α-imino-p-methylbenzyl)-4-hydroxy-6-phenyl-1-methyl-2(1H)-pyridone,
(d) 3-(α-imino-p-methoxybenzyl)-4-hydroxy-6-phenyl-1-methyl-2(1H)-pyridone,
(e) 3-(α-imino-m-trifluoromethylbenzyl)-4-hydroxy-6-phenyl-1-methyl-2(1H)-pyridone,
(f) 3-(α-iminobenzyl)-4-hydroxy-6-(p-chlorophenyl)-1-methyl-2(1H)-pyridone,
(g) 3-(α-iminobenzyl)-4-hydroxy-6-(p-fluorophenyl)-1-methyl-2(1H)-pyridone,
(h) 3-(α-iminobenzyl)-4-hydroxy-6-(p-tolyl)-1-methyl-2(1H)-pyridone,
(i) 3-(α-iminobenzyl)-4-hydroxy-6-(p-anisyl)-1-methyl-2(1H)-pyridone, (j) 3-(α-iminobenzyl)-4-hydroxy-6-(m-trifluoromethyl-phenyl)-1-methyl-2(1H)-pyridone,
(k) 3-(α-iminobenzyl)-4-hydroxy-6-(o-tolyl)-1-methyl-2(1H)-pyridone,
(l) 3-(α-iminobenzyl)-4-hydroxy-6-(3,4-dichloro-phenyl)-1-methyl-2(1H)-pyridone,
(m) 3-(α-imino-p-chlorobenzyl)-4-hydroxy-6-(p-chloro-phenyl)-1-methyl-2(1H)-pyridone,
(n) 3-(α-imino-p-fluorobenzyl)-4-hydroxy-6-(p-fluoro-phenyl)-1-methyl-2(1H)-pyridone,
(o) 3-(α-imino-o-fluorobenzyl)-4-hydroxy-6-(p-fluoro-phenyl)-1-methyl-2(1H)-pyridone,
(p) 3-(α-iminobenzyl)-4-hydroxy-6-(3,4-difluoro-phenyl)-1-methyl-2(1H)-pyridone, or
(q) 3-(α-imino-o-fluorobenzyl)-4-hydroxy-6-phenyl-1-methyl-2(1H)-pyridone, respectively.

The 3-(α-iminobenzyl)-4-hydroxy-6-phenyl-1-methyl-2(1H)-pyridone of this example is an effective minor tranquilizer when orally administered to an animal in need of said treatment at a dosage of 100 mg. two to four times per day. The compound of this example is also effective as a sleep inducer when orally administered to an animal in need of said treatment at a dosage of 200 mg. just before bedtime.

Furthermore, the 3-(α-imino-p-fluorobenzyl)-4-hydroxy-6-phenyl-1-methyl-2(1H)-pyridone of this example is an effective muscle-relaxant when orally administered to an animal in need of said treatment at a dosage of 100 milligrams two to four times per day.

What is claimed is:
1. A compound of the formula

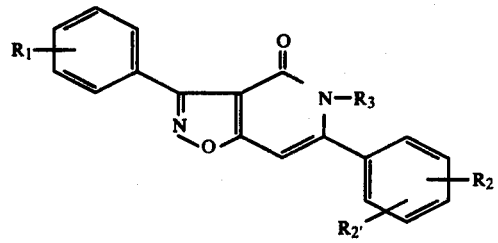

where
$R_1$, $R_2$ and $R_2'$ each independently represent hydrogen, halo having an atomic weight of about 19 to 36, lower alkyl, lower alkoxy or trifluoromethyl, and
$R_3$ represents lower alkyl.
2. The compound of claim 1 which is 5-methyl-3-(p-fluorophenyl)-6-phenyl-isoxazolo[4,5-c]pyridin-4-(5H)-one.

* * * * *